United States Patent
Douplik et al.

(10) Patent No.: US 9,295,392 B2
(45) Date of Patent: Mar. 29, 2016

(54) METHOD FOR IDENTIFYING MALIGNANCIES IN BARRETT'S ESOPHAGUS USING WHITE LIGHT ENDOSCOPY

(71) Applicant: NOVADAQ TECHNOLOGIES INC., Mississauga, CA (US)

(72) Inventors: Alexandre Douplik, Erlangen (DE); Desmond C. Adler, Melrose, MA (US); Brian C. Wilson, Toronto (CA); Norman Marcon, Toronto (CA)

(73) Assignee: NOVADAQ TECHNOLOGIES INC., Mississauga (CA)

( * ) Notice: Subject to any disclaimer, the term of this patent is extended or adjusted under 35 U.S.C. 154(b) by 0 days.

(21) Appl. No.: 13/625,867

(22) Filed: Sep. 24, 2012

(65) Prior Publication Data
US 2013/0178748 A1   Jul. 11, 2013

Related U.S. Application Data

(63) Continuation of application No. 12/572,473, filed on Oct. 2, 2009, now abandoned.

(60) Provisional application No. 61/102,091, filed on Oct. 2, 2008.

(51) Int. Cl.
*A61B 6/00* (2006.01)
*A61B 5/00* (2006.01)
*A61B 1/04* (2006.01)

(52) U.S. Cl.
CPC ............ *A61B 5/0075* (2013.01); *A61B 5/0071* (2013.01); *A61B 5/0084* (2013.01); *A61B 5/4233* (2013.01); *A61B 1/043* (2013.01)

(58) Field of Classification Search
USPC .......................... 600/407, 473, 476
See application file for complete search history.

(56) References Cited

U.S. PATENT DOCUMENTS

| | | | |
|---|---|---|---|
| 6,922,583 B1* | 7/2005 | Perelman et al. | 600/476 |
| 2002/0143243 A1* | 10/2002 | Georgakoudi et al. | 600/310 |
| 2007/0177152 A1* | 8/2007 | Tearney et al. | 356/477 |

OTHER PUBLICATIONS

Georgakoudi et al., "Chapter 31: Quantitative Characterization of Biological Tissue Using Optical Spectroscopy." Copyrighted 2003 by CRC Press LLC., pp. 1-33.*
Dawson et al., "Theoretical and Experimental Study of Light Absorption and Scattering by In Vivo Skin," 1980, The Institute of Physics, pp. 695-709.*
Georgakoudi et al., "Characterization of Dyplastic Tissue Morpology and Biochemistry in Barret's Esophagus using Diffuse Reflectance and Light Scattering Spectroscopy," 2005, pp. 100-105.*

\* cited by examiner

*Primary Examiner* — James Kish
(74) *Attorney, Agent, or Firm* — Oliff PLC

(57) ABSTRACT

A method is described for computing a statistically significant difference between dysplasia and Barrett's esophagus (both with and without inflammatory component) using a discriminate function with diffuse reflectance measurements performed at a minimum of four different wavelengths of 485, 513, 598, and 629 nm. The discriminate function found depends both on local blood fraction volume $T_{HB}$ and oxygenation $SO_2$. A pull-back approach of spectral data acquisition is disclosed which takes into account tissue motility in esophagus and measurement geometry peculiarities. The pull-back approach provides a significant improvement of measurement reproducibility and reduction of data deviation by 75-100%, resulting in a better discrimination between different histological groups.

20 Claims, 3 Drawing Sheets

METHOD FOR IDENTIFYING MALIGNANCIES IN BARRETT'S ESOPHAGUS USING WHITE LIGHT ENDOSCOPY

CROSS-REFERENCE TO RELATED APPLICATIONS

This application is a continuation of U.S. patent application Ser. No. 12/572,473, filed on Oct. 2, 2009, pending, which claims priority to U.S. Provisional Application Ser. No. 61/102,091, filed Oct. 2, 2008, the entire contents of which are incorporated herein by reference.

FIELD OF THE INVENTION

The invention relates to white light endoscopy to guide the biopsy collection, and more particularly to detecting an intrinsic optical signature of early cancer lesions in Barrett's esophagus (BE) using diffuse reflectance spectroscopy, without staining or dying to enhance malignant/non-malignant contrast.

BACKGROUND OF THE INVENTION

Gastrointestinal (GI) malignancies continue to be the second leading cause of cancer-related deaths in the United States (24%). One of the highest shares in GI malignancies belongs to esophagus cancer (10% or 12000-14000 per year based on 2000-2003 statistics). People from the Western hemisphere tend to develop esophageal cancer based on prior metaplastic mucosal transformation often called as Barrett's esophagus (BE). Barrett's esophagus is a cancer risk factor and frequently linked to the preexisting gastro-esophageal reflux disease (GERD). Patients with Barrett's esophagus have a 30-125 fold higher risk of developing cancer of the esophagus than the general population.

Several diagnostic methods exist that do not use any external dyes, such as autofluorescence spectroscopy and imaging, narrow band imaging, Raman spectroscopy, Optical Coherence Tomography and Doppler Optical Coherence Tomography, Laser Scattering Spectroscopy, confocal endoscopy, Infrared Endoscopy. Other methods that use external dyes and staining in vivo include chromo-endoscopy, magnification chromo-endoscopy, and fluorescence imaging of ALA-5 staining.

Recently developed methods are either small field of view and, consequently, very time consuming (Raman spectroscopy, Optical Coherence Tomography, Doppler Optical Coherence Tomography, Laser Scattering Spectroscopy, confocal endoscopy) or require application of external dyes (chromo-endoscopy, fluorescence imaging of ALA-5 staining) Narrow band imaging and near-infrared multimodal endoscopy methods were reported just within last two years and still required to prove its sensitivity and specificity abilities. The narrow band imaging is based on recognizing the irregular pit pattern epithelium islands within areas of intestinal metaplasia. This approach can be significantly affected by human factor and heavily relies upon extensive training of the endoscopist performing the examination.

Accordingly, there is a need for a clinically recognized real-time, large field-of-view screening method to discriminate dysplasia from metaplasia in Barrett's Esophagus.

BRIEF SUMMARY OF THE INVENTION

The developed method uses a diffuse reflectance collected within visible range at wide field illumination and point measurement. A set of at least four distinctive wavelength ranges has been found to facilitate the malignant/non-malignant contrast. The discriminating algorithm is based on a linear polynomial function B4 providing 77% of sensitivity and 81% of specificity based on the results obtained from the clinical study on 32 patients including 7 with displasia found.

An optimal result discriminate function B4 is based on diffuse reflectance Rd measured at 4 wavelengths—485±5, 513±5, 598±2, 629±5 nm.

$$B4 = -14.32 + 626.88 \cdot Rd_{485} - 721.31 \cdot Rd_{513} + 253.76 \cdot Rd_{598} + 75.16 \cdot Rd_{629}$$

The discriminate function found is directly proportional to oxygenation $SO_2$ and inversely proportional to local blood fraction volume $T_{HB}$. B4 values computed from the dysplastic data are significantly lower than that of the BE or BE with inflammatory component (BEI). The discrimination between BE without inflammation background and dysplasia is more distinct than that of BE with inflammatory component (BEI) versus dysplasia.

The discrimination between BE and dysplasia can be slightly improved by 2-2.5% in terms of Area under ROC curve (AUC) by adding into the discriminate function another wavelength: 501±5 nm. At the same time, if one of the four wavelengths found for the B4 function is excluded, the discrimination BE versus Dysplasia will be drastically reduced from 77% to 61% (in terms of AUC).

DETAILED DESCRIPTION OF THE INVENTION

Figure 1:
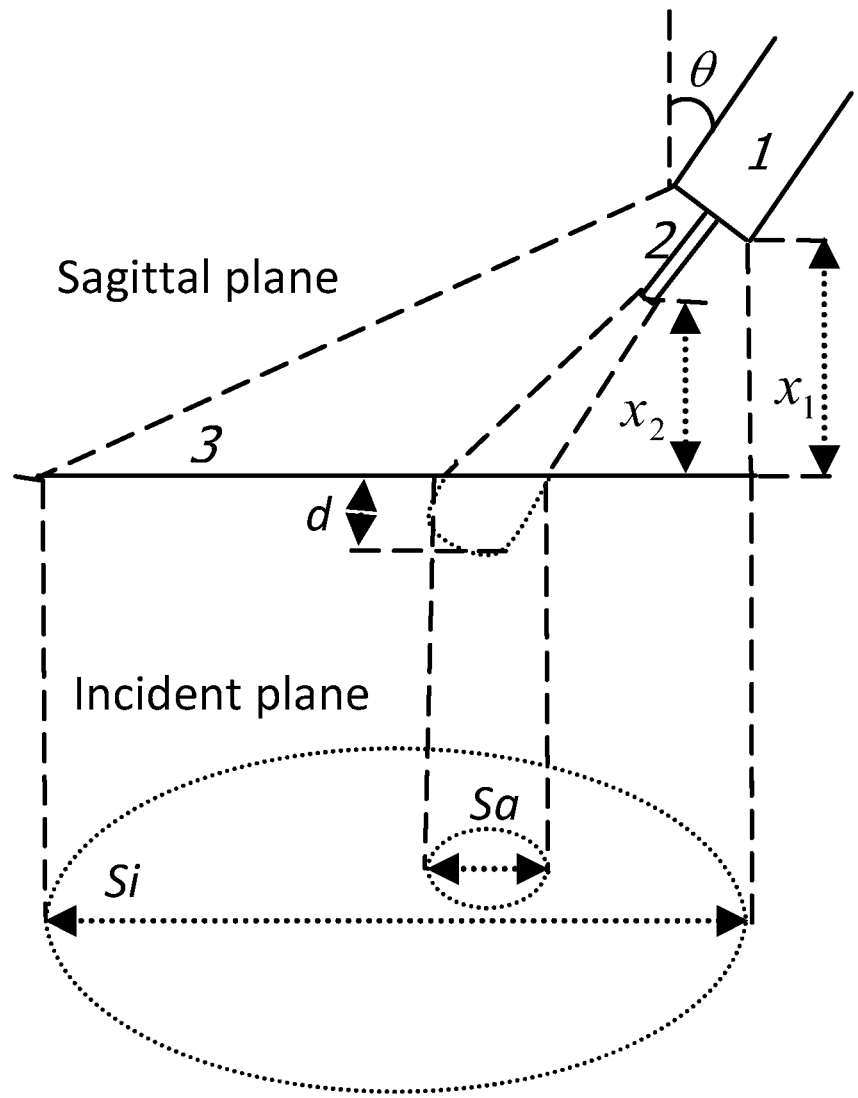
FIG. 1 shows the illumination geometry for diffuse reflectance imaging.

An adjuvant screening technique is described which is compatible with conventional white light endoscopy to guide the biopsy collection in Barrett's esophagus (BE) in real time. By systematic analysis of the diffuse reflectance spectra, we have found a specific algorithm, that provides statistically-significant discrimination between BE and dysplasia, with or without the presence of an inflammatory component.

An understanding of the blood microcirculation in tumors is important for their detection, diagnosis and treatment. Relatively high values of blood supply in tumors are associated with increased metabolism and aggressiveness. Increase of blood supply provides a growing cancerous tissue with additional nutrients via growth of new vasculature through a mechanism called angiogenesis. Typical development of epithelial-originating cancers occurs in several sequential stages—low grade dysplasia or pre-cancer, high grade dysplasia, carcinoma in situ, invasive cancer, and finally metastatic spread beyond the primary location. Metastatic disease has poor prognosis; thus, early detection of cancer may improve patient survival.

The role of angiogenesis in the early stages of cancer development is still unclear, with recent publications proposing contradictory theories. However, it is assumed that, even in low grade dysplasia, deregulated mitotic processes require an increase in blood supply. This leads, in turn, to an increase in both vascular density and local hemoglobin concentration or fractional blood volume within the malignant lesion.

The goal of the study was to create an adjuvant screening technique compatible with conventional white light endoscopy to guide the biopsy collection in Barrett's esophagus in real time. The current objectives of the study focus on finding the intrinsic optical signature of early cancer lesions in BE not using any additional staining or dyes to enhance malignant/non-malignant contrast. The main assumption is that in case of dysplastic tissue the higher oxygen/nutrients demand and possible leakage of premature tumor local blood micro-vessels would lead to higher local concentration of blood. The working hypothesis presumes also that the local distribution of blood will be altered in dysplastic lesions that may lead to reduced efficiency of oxygen/nutrients supply and ultimately to reduced blood oxygenation level depending on development phase of dysplasia.

In general case of endoscopic measurements, the measured signal on the probe is composed by specular reflection and diffuse reflection of the tissue.

Specular (Fresnel) reflection is caused by mismatch of index of refraction on the air/tissue border. This reflectance is particularly important for normal (or close to normal) position of endoscope. In this case the specular coefficient of reflection can be as large as 2-4%. In other geometries specular reflection is minimal and can be ignored.

Light not reflected on the surface of the tissue first interacts with epithelium layer. The nuclei of the epithelial cells have higher refractive index than the surrounding cytoplasm, and hence act as light scatterers.

The size of the nuclei in the normal epithelium is 4-7 µm, which conditions strongly forward scattering with anisotropy factor in 0.98-0.99 range. In dysplastic epithelium the nuclei become pleomorphic, crowded, hyperchromatic and occupy almost the whole cell (diameter 10-20 µm). These morphological changes in nuclei during dysplastic transformation and corresponding peculiarities of the epithelial scattering were used in polarized light scattering spectroscopy and field-based light scattering spectroscopy to separate between normal and dysplastic epithelium.

Such as there are no significant absorbers in the epithelium layer, thus, even despite its thickness (200 µm), most of light propagates through the layer and penetrates into the lamina propria. The scattering in this layer is caused mainly by fine collagen fibrils and subcellular organelles (<1 µm, which conditions strong backscattering). The absorption in this layer is mainly caused by the presence of capillaries, which supply blood circulation.

After significant scattering and absorption in mucosa layer the remaining part of the light penetrates in the submucosa. The submucosa is composed almost entirely of a dense network of larger collagen fibers. The significant diameter of these fibers (several microns) conditions strongly forward scattering. Large blood vessels cause significant absorption of light in this layer.

The fraction of the incident light that is not absorbed or backscattered in the previous two layers enters muscularis propia where it gets further strongly absorbed by blood and scattered.

Finally, light transmitted through the thick muscular layer into deeper tissues is confined mainly to the red range of the spectra and does not significantly affect the reflected flow. Simple 2-layer models of the esophageal wall have shown that in the infra-red range (650-750 nm) the absorption of blood is negligible. Taking into account that own absorption of tissue in this region is still less than the reduced coefficient of scattering, one can expect scattering-dominated light propagation regime in the tissue. In this case, the coefficient of reflection will be close to 0.5 (in the absence of absorption half of light penetrates into deeper tissues where it will be finally absorbed, another half will emerge on the surface of the tissue). Thus, the signal in this range is not sensitive to the blood content, and one can use this region to normalize spectra to take into account the conditions of the measurement.

For blue and green ranges, $\mu_a/\mu_s>1$, with light propagation dominated by absorption. In this case the absorption is significant and the signal in this range will be quite sensitive to the blood content. $\mu_a$ is here the coefficient of absorption and, and $\mu_s$ is the reduced coefficient of scattering.

Two geometries are commonly used during diffuse reflectance spectroscopy in vivo:

(1) A point-illumination—point-detection geometry: the sampling light is delivered through a single optical fiber to the tissue and the reflectance signal is detected by a radially displaced pick-up fiber.

(2) A wide-field illumination and point-detection geometry or imaging illumination geometry: the light from the source is delivered through the endoscope's light guides illuminating a large area of the tissue surface, and a single pick-up fiber or a bundle of pick-up fibers approach the tissue via the biopsy channel of the endoscope.

Preliminary considerations have show that the imaging illumination geometry can make diffuse reflectance more compatible with endoscopic imaging than the "point illumination—point detection geometry." The imaging illumination geometry setup is shown in FIG. 1 where 1 represents the endoscope; 2 the fiber probe; 3 the incident (tissue) surface; $x_1$ the distance between the endoscope tip and tissue surface; θ the incline angle of the collecting fiber and normal to the incident surface; $x_2$ the distance between the diffuse reflectance probe tip and tissue surface; d the diffuse reflectance interrogating depth; Sa the diffuse reflectance collection area on the incident surface; Si the area illuminated by the endoscope light source on the incident surface; $\phi_1$ the NA of the endoscope's light guide; $\phi_2$ the NA of the collecting probe; and τ the twisting angle.

A xenon lamp (Olympus) from the endoscopic light source and fiberoptic spectrometer (MedSpecLab, MSL-CS1-USB-VR®), and reflectance probe (0.6 mm diameter fiber bundle including 200 micron central emission silica fiber surrounded by six 200 micron silica collection fibers) were used to measure the diffuse reflectance spectra at the clinical study. The surrounding fibers of the reflection probe were arranged in a vertical row to form a "spectral slit" entering the spectrometer.

The angle of incidence of the source fiber(s) on the surface (θ) was 35-45°. The distance $x_1$ was set at 1 cm for imaging illumination geometry. $x_2$ varied from 0 to 5 mm. $S_i$ was greater than $S_a$ by at least an order of magnitude. NA of the endoscope's light guide is 0.57 and NA of the collecting probe is 0.22.

Figure 2:
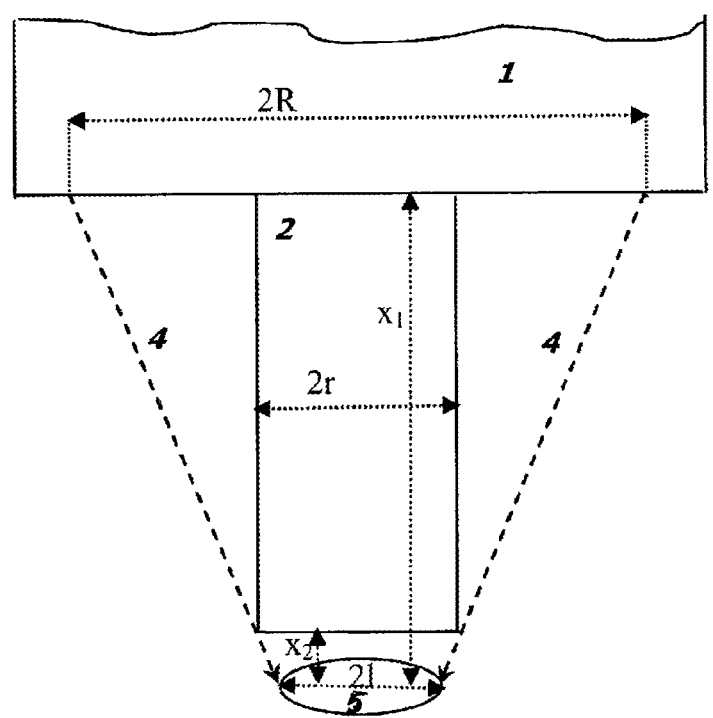
FIG. 2 shows a shadow effect during endoscopic diffuse reflectance measurements.

It has been observed that the reflectance measurements depend on the location of the fiber probe in relation to the tissue due to the complex measurement geometry and high motility GI environment. As illustrated in FIG. 2, when the probe is located just above the surface of the tissue, some surface regions may be shadowed by the tip of the fiber. These differences in geometry may initiate changes in the shape of reflectance spectra and camouflage the specific spectral signature of dysplasia. The light flux remitted from the esophagus is affected by changes in geometry due to movement from peristalsis/spasm or pulse/breathing, peculiarities of the tissue, interpatient variability and human factor related to the particular endoscopist manner of examination. In particular, the amplitude of reflected signal depends on the endoscope-probe-tissue distances and angle. Different distances from the tissue lead to different illumination of the surface and different sampling areas and as a result to different levels of the measured signal.

The endoscope with the source of light is held at a certain distance to the surface (10-15 mm), while the fiber can be dragged back and forth through the biopsy channel of the endoscope. Apparently, there is an obvious geometrical limitation on the distance $x_2$: $0 < x_2 < x_1$ It will be assumed that the endoscope (with radius of source of light—R) is positioned normally to the tissue on the height, while the fiber with radius r can be positioned at any height $x_2$ ($0 < x_2 < x_1$) above the tissue. In FIG. 2, reference symbol 5 indicates the shadow on the incident (tissue) surface 3 (FIG. 1); reference symbol 4 the endoscopic light source aperture; 2R the distance between the light guides (centers) on the endoscope tip; and r the reflectance probe radius. Otherwise, the reference symbols of FIG. 1 apply also to FIG. 2. The shadow disappears at $x_2^0 = x_1 * r/R$ which for the exemplary experimental geometry (r=0.3 mm, R=5 mm, $x_1$=10-15 mm) $x_2^0$ can be estimated as 0.6-0.9 mm, i.e. the shadow disappears within the first mm of $x_2$. Fluctuation of $x_2$ may result in profound changes in measured spectra, whereas the spectra collected are stable within certain ranges of $x_1$ and $\theta$, and are not significantly affected by $\tau$. At the same time, even subtle variations of $x_2$ may significantly impact the shape and amplitude of the reflected spectra. Thus, the parameter $x_2$ is the most critical for reproducibility of diffuse reflectance spectra acquired in esophagus and should be carefully controlled.

A special measurement approach has been developed in order to take into account $x_2$. This approach, that is termed "pullback routine," comprises lifting up the optical probe from the tissue surface up to 4-5 mm above while the spectral data is being acquired all the way up. As a rule, data collection at a single pullback routine provides acquisition of 20-30 spectra. Between three and four pull back routines are carried out from every tissue spot. The spectra collected which are free from the shadowing effects are extracted from the entire data set. Usually, these are the spectra collected within 2-5 mm above the tissue in terms of ("above" spectra). The extraction algorithm is based on grouping and normalizing the spectra according by the spectral integral 620-630 nm. Red range is expected to be the worst $\lambda_w$ to discriminate cancerous from noncancerous due to its weak absorption of blood. Hence, this range is used as a denominator to reduce interpatient variance and geometrical conditions differences. The pullback routine allows significantly reducing the spectral data variance within 460-630 nm.

A method will now be described for classifying tissues into two distinct classes—dysplastic and non-dysplastic based on their reflectance spectra. The study focuses on separation of Barrett's esophagus spots vs. dysplastic tissue.

Statistical methods can be employed, including discriminate function analysis (DA), logistic regression, principal components analysis, and factor analysis. Although principal components analysis and logistic regression have some advantages over DA, Discriminant Analysis was selected due to its transparent physical interpretation for ultimate implementation into clinical technique using minimal number of wavelengths.

Discriminant Analysis (DA) and multiple Discriminant Analysis (MDA) are used to separate two (DA) or more (MDA) groups of data, where each data point is characterized by a set of independent variables. A single data point (case) consists in the exemplary embodiment of the pre-processed spectrum for a single tissue site. The independent variables are the light intensities measured at each wavelength from 450 nm-630 nm resolved by 1 nm. Data were grouped by a clinical pathologist into normal esophagus (NE), Barrett's Esophagus (BE), Barrett's Esophagus with inflammatory component (BEI), low-grade dysplasia (LGD), high-grade dysplasia (HGD), and invasive carcinoma (CA). NE and CA were excluded from our consideration according to the main objective of the study: discriminating early cancer lesions at Barrett's esophagus.

DA (MDA) is closely related to a multivariate analysis of variance (MANOVA). Discriminant Analysis is merely an inverse of a one-way MANOVA. The levels of the independent variable (or factor) for Manova become the categories of the dependent variable for Discriminant Analysis, and the dependent variables of MANOVA become the predictors for Discriminant Analysis. Based on the user-supplied group classifications for each spectrum, DA (MDA) seeks to produce a set of linear combinations that maximizes the differences between the values of the dependent variables in different groups. Each linear combination is embodied by a discriminate function of length N with coefficients $c_{k,n}$. After applying a discriminate function to a given reflectance spectrum $S(\lambda)$, the result is a canonical variable (score) y. Such as the number of discriminate functions is lesser of M−1 (where M is a number of groups) and the number of independent variables N, it is possible to generate min (N,M−1) canonical variables $y_k$ for each reflectance spectrum.

$$y_k = \sum_{n=1}^{N} c_{n,k} S(\lambda_n),$$

If the data groups are significantly different in terms of their spectral shape, the resulting canonical variables will tend to cluster in distinct regions for each group. If only two groups are used in the analysis (e.g., BE/BEI vs. LGD/HGD) then only one canonical variable (k=1) will be required to distinguish the groups.

By examining the discriminate function coefficients $c_n$, it is possible to determine which wavelength regions are the most relevant for providing contrast between the data groups. Regions with largest coefficients correspond to the most specific data, whereas small coefficients are less significant.

The ability of the Discriminant Analysis to extract discriminate functions suitable for producing accurate classifications is enhanced by adequate sample size and homoscedasticity (homogeneity of variances). The variance of each independent variable has to be similar between the sample groups. Validity of this assumption can be seen in Table 1 where the data on standard deviation within BE+BEI (group 0) and LGD+HGD (group 1) is summarized for the three selected wavelengths 485, 513, and 598 nm.

TABLE 1

| Group | Wavelength | | |
|---|---|---|---|
| | 485 nm | 513 nm | 598 nm |
| 0 (BE + BEI) | 0.0078 | 0.0087 | 0.0104 |
| 1 (LGD + HGD) | 0.0072 | 0.0076 | 0.0083 |

The study population included patients referred to St. Michael's Hospital Endoscopy Unit for esophagogastroduodenoscopy (EGD). All patients recruited for the autofluorescence study were patients who required endoscopy as clinically indicated for diagnosis, surveillance or treatment. Normal subjects, or persons not otherwise requiring endoscopy, were not recruited for the purposes of the study. Patients were informed of the study and received an explanation of study procedures by the principal investigator (PI). Informed consent was obtained from all subjects prior to endoscopy.

All adult patients booked for diagnostic, surveillance or therapeutic EGD or colonoscopy who consented to participate in this study and did not have one or more of the following exclusion criteria below, were included.

Age <18 years; unable or unwilling to give informed consent were not included.

Ionizing radiation therapy to the chest or abdomen within the past six months.

Dye-staining of the esophagus within the past 7 days.

Significant esophageal bleeding of any etiology.

Concurrent esophageal candidiasis.

Patients who are receiving or have received cytotoxic chemotherapy or chemopreventive drugs for cancer within three months.

Patients who have received fluorescent photosensitizing drugs (such as PHOTOFRIN®) within three months.

Patients who have used sucralfates or liquid antacids within 24 hours prior.

The study included 32 patients in total over a 3-year enrolment period (2004-2006).

We have collected 5 histological groups—normal esophagus (NE), normal esophagus with inflammatory component (NEI), Barrett's esophagus (BE), Barrett's esophagus with inflammatory process (BEI), Low Grade Dysplasia (LGD), High Grade Dysplasia (HGD). Only last four groups were taken for analysis to find out cancerous/noncancerous discrimination.

BE (group 0)–28 spots (791 (training)+518 (test) 1309 spectra)

BEI (group 2)–20 spots (244 (training)+439 (test) 683 spectra)

LGD–9 spots (181 (training)+86 (test) 267 spectra)

HGD–7 spots (86 (training)+234 (test) 320 spectra)

LGD and HGD groups have been merged into one "D" group (group 1) due to limited number of cancerous spots collected.

The developed method uses a diffuse reflectance collected within visible range at wide field illumination and point measurement not using any additional staining or dyes. A set of four distinctive wavelength ranges (which include the three wavelengths listed in Table 1) has been found to facilitate the malignant/non-malignant contrast. The discriminating algorithm is based on a linear polynomial function B4 providing 77% of sensitivity and 81% of specificity based on the results obtained from the clinical study on 32 patients including 7 with displasia found.

A result discriminate function B4 is based on diffuse reflectance Rd measured at 4 wavelengths—485±5, 513±5, 598±2, 629±5 nm $$B4 = -14.32 + 626.88 * Rd_{485} - 721.31 * Rd_{513} + 253.76 * Rd_{598} + 75.16 * Rd_{629}$$

The discriminate function found is directly proportional to oxygenation of $SO_2$ and inversely proportional to local blood fraction volume THB. B4 values computed from the dysplastic data are significantly lower than that of the BE or BE with inflammatory component (BEI). A useful threshold value for distinguishing between dysplasia and nondysplasia (BE+BEI) was found to be $B4_{thres} = -0.8$, with values of $B4 < -0.8$ classified as dysplasia and $B4 > -0.8$ classified as non-dysplastic tissue. The discrimination between BE without inflammation background and dysplasia is more distinct than that of BE with inflammatory component (BEI) versus dysplasia.

Figure 3:
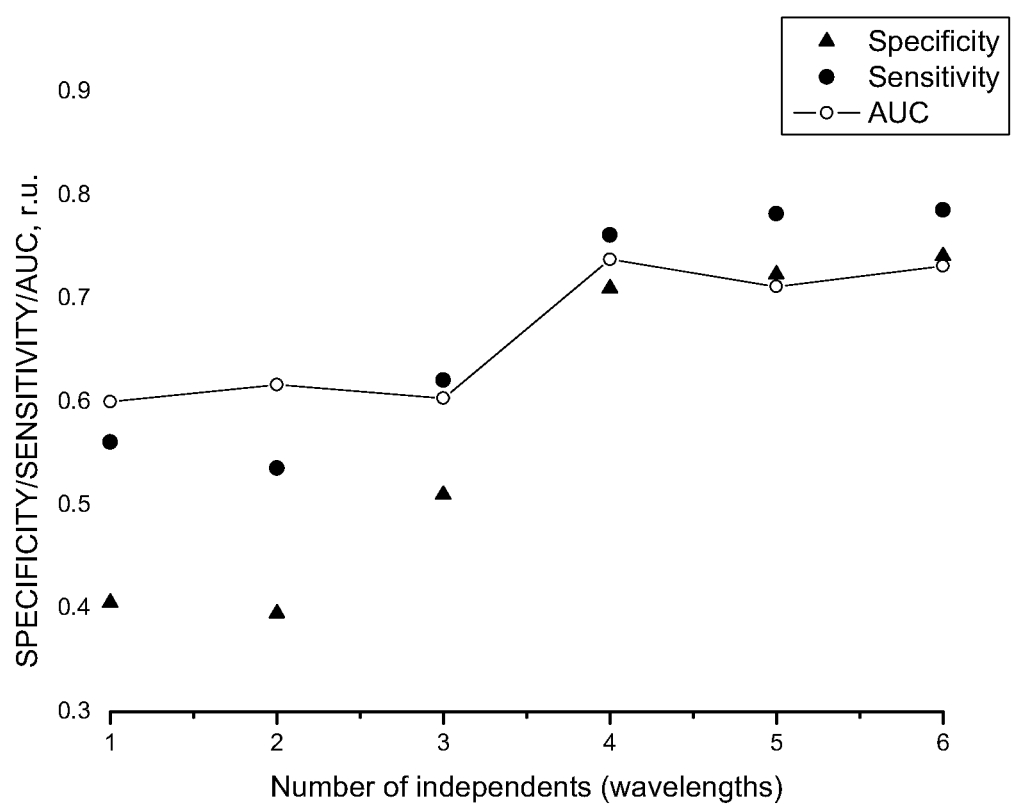
FIG. 3 shows the dependence between specificity/sensitivity provided by the discriminate function B and the number of wavelengths participating in the discriminate function.

The minimum number of wavelengths required to provide the highest specificity/sensitivity has been found to be four, as shown in FIG. 3 and described with reference to Table 2 below. FIG. 3 shows the dependence between specificity/sensitivity provided by the discriminate function B and number of wavelength participating in the discrimination function. The line is just a guide for the eye. The set of four wavelengths provides the highest specificity/sensitivity because the most substantial difference is between discriminating power of three (485, 598, 629 nm) and four wavelengths (485, 513, 598, 629 nm).

TABLE 2

| Wavelength | Function B1 | Function B2 | Function B3 | Function B4 | Function B5 | Function B6 |
|---|---|---|---|---|---|---|
| Constant (C) | -1.33469 | -6.0054 | -9.7687057 | -14.3225 | -12.8803 | -16.0918 |
| 485 | 135.2218 | 145.2608 | 36.1187989 | 626.8844 | 901.9895 | 1027.081 |
| 629 | | 40.8738 | 57.8663474 | 75.15688 | 67.68892 | 82.73592 |
| 598 | | | 98.794127 | 253.7611 | 241.0908 | 373.5058 |
| 513 | | | | -721.309 | -424.382 | 76.29472 |
| 501 | | | | | -545.793 | -1017.41 |
| 590 | | | | | | -309.954 |

The wavelengths and discriminate functions obtained on a training dataset are shown in Table 2. It is noteworthy to point to the value of the constant C in Table 2 which is an offset parameter used to center groups (dysplasia vs. non-dysplasia) and reflects the influence of random factors upon the discriminate function. By design, the threshold should be 0. However, it was found that a more balanced separation (for averaged per spot spectra) can be attained by setting the threshold to -0.8, which is possible when using the LDA method.

C is always much lower (at least by a factor of 5) than any of the contribution coefficients of the corresponding wavelength set.

The discrimination between BE and dysplasia can be slightly improved by 2-2.5% in terms of Area under ROC curve (AUC) by adding into the discriminate function another wavelength: 501±5 nm, as evident from Table 2. However, it should be noted that if one of the four wavelengths found for the B4 function is excluded, the discrimination BE versus Dysplasia will be dramatically reduced from 77% to 61% (in terms of AUC).

The local blood perfusion condition anticipated for a tumor is a combination of high hemoglobin concentration and low blood oxygenation. Therefore, a lower value of B4 is expected within the tumor compared to the adjacent normal tissue. For instance for tumors of the lungs, the local blood fraction is increased by a factor of 2.3, while blood oxygenation drops from 0.92 to 0.49. Considering this case as an example, B4 can be expected to provide a contrast between normal tissue and tumor as 1:0.22.

B4 is inversely highly dependent on both total hemoglobin and oxygenation. The higher the B4 parameter, the lower is both local concentration of total hemoglobin and blood oxygenation.

In conclusion, a statistically significant difference has been found between dysplasia and Barrett's esophagus (both with and without inflammatory component) by using a discriminate function using 485, 513, 598, and 629 nm with a tolerance range ±5 nm. The discriminate function found depends both on local blood fraction volume $T_{HB}$ and oxygenation $SO_2$. The discrimination between BE without inflammation background and dysplasia is more distinct than that of BE with inflammatory component (BEI) versus dysplasia. The $T_{HB}$ and $SO_2$ peculiarities determined via the green range have not been identified as statistically relevant criteria to provide a contrast between dysplastic and metaplastic tissues at Barrett's esophagus while the usage of Blue (485 and 513 nm) and Red (598 and 629 nm) bands facilitate a significant sensitivity and specificity despite the fact that the spectral signature of hemoglobin/oxyhemoglobin within 530-580 nm is much more obvious. This result is unexpected and could not be predicted from the theoretical standpoint based on hemoglobin absorption spectra. The blue/red optimal discrimination can be based on peculiarities of the diffuse reflectance sampling depth in Barrett's esophagus related, in turn, to data specificity of displastic optical signature. The results have shown that the procedure design at diffuse reflectance spectra collection is important. An original pull back approach of spectral data acquisition has been developed to take into account tissue motility in esophagus and measurement geometry peculiarities. The pull back approach provided a significant improvement of measurement reproducibility and reduction of data deviation by 75-100%. This, in turn, led to a better discrimination between different histological groups during the study.

The studies reported herein improve the diagnostic accuracy of autofluorescence endoscopy in Barrett's esophagus. Hence, one possible implementation would be to combine 4-channel reflectance imaging with autofluorescence endoscopy. It is important to note that the algorithm developed here exploits a different spectral range from that used currently in autofluorescence endoscopy systems that use primarily the green (~490-570 nm) range for the autofluorescence emission with the recent technology (Onco-LIFE®).

The blue and red discriminating wavelengths found do not interfere with most of the green band reserved for the autofluorescence acquisition. Hence, one can assume that the correlation between reflectance and fluorescence data should not be high. If the latter assumption is correct, then both the sensitivity and specificity provided by the diffuse reflectance can be improved by the autofluorescence data when both reflectance and fluorescence are used simultaneously. Hence, the two techniques are spectrally compatible and potentially provide complementary information.

The method of the invention is not limited to Barrett's esophagus, but can also be applied in vivo in other organs and tissues. A combined spectral imaging method incorporating the method of the invention can be used to guide the random biopsy at Barrett's metaplastic transformation to improve early cancer diagnostics in the esophagus.

While the invention is receptive to various modifications, and alternative forms, specific examples thereof have been shown in the drawings and are herein described in detail. It should be understood, however, that the invention is not limited to the particular forms or methods disclosed, but to the contrary, the invention is meant to cover all modifications, equivalents, and alternatives falling with the spirit and scope of the appended claims.

The invention claimed is:

1. A method for assessing cancer risk by diffuse reflectance spectroscopy, comprising:
    directing light from a source to an area of esophageal tissue with an endoscope to provide wide field illumination of a surface of the tissue, the light having a wavelength range that includes at least a portion of the visible spectrum;
    measuring, with a reflectance probe, intensity of diffusely reflected light in at least four distinct narrow wavelength bands at different tissue sampling sites, said at least four bands being in the wavelength range of the illumination light, two of said bands being in the blue light range, and two of said bands being in the red light range;
    computing a parameter value for each of the different tissue sampling sites, the parameter being a predetermined linear discriminate function based on said intensity measurements; and
    assessing malignancy of the tissue based on the computed parameter values from the different tissue sampling sites.

2. The method of claim 1, wherein the at least four distinct narrow wavelength bands include the wavelengths 485±5 nm, 513±5 nm, 598±5 nm, and 629±5 nm.

3. The method of claim 2, wherein the discriminate function is $$B4 = -14.32 + 626.88 * Rd_{485} - 721.31 * Rd_{513} + 253.76 * Rd_{598} + 75.16 * Rd_{629},$$

wherein $Rd_{485}$ is diffuse reflectance measured at 485±5 nm, $Rd_{513}$ is diffuse reflectance measured at 513±5 nm, $Rd_{598}$ is diffuse reflectance measured at 598±5 nm, $Rd_{629}$ is diffuse reflectance measured at 629±5 nm, and the computed parameter value is represented by B4.

4. The method of claim 3, wherein the diffuse reflectance measured at 485±5 nm, 513±5 nm, 598±5 nm, and 629±5 nm is normalized with respect to reflectance in the infrared wavelength range (650-750 nm) where absorption of blood is negligible.

5. The method of claim 1, further comprising
    placing the reflectance probe in close proximity to the tissue surface at one of said sampling sites and then carrying out said measuring; and
    lifting the reflectance probe (pull-back) from said close proximity to the tissue surface to a distance where the reflectance probe no longer shadows the tissue and then repeating said measuring.

6. The method of claim 5, wherein the lifting is repeated at least once for a tissue spot, said measuring being repeated after each lifting.

7. The method of claim 1, wherein the blue light range is 470-520 nm, and the red light range is 590-650 nm.

8. The method of claim 1, wherein said directing light from the source to the area of esophageal tissue comprises directing light through a light guide of the endoscope.

9. A real-time method for assessing cancer risk by diffuse reflectance spectroscopy, comprising:
    directing light from a source to an area of esophageal tissue with an endoscope to provide wide field illumination of a surface of the tissue, the light having a wavelength range that includes at least a portion of the visible spectrum;
    measuring, with a reflectance probe, intensity of a diffusely reflected light in at least four distinct narrow wavelength bands at different tissue sampling sites, said at least four bands being in the wavelength range of the illumination light, two of said bands being the blue light range, and two of said bands being in the red light range;

computing, via a processor, a parameter value for each of the different tissue sampling sites, the parameter being a predetermined linear discriminate function based on said intensity measurements; and assessing malignancy of the tissue based on the computed parameter values from the different tissue sampling sites.

10. The method of claim 9, wherein the at least four distinct narrow wavelength bands include the wavelengths 485±5 nm, 513±5 nm, 598±5 nm, and 629±5 nm.

11. The method of claim 10, wherein the discriminate function is $$B4 = -14.32 + 626.88*Rd_{485} - 721.31*Rd_{533} + 253.76*Rd_{598} + 75.16*Rd_{629},$$

wherein $Rd_{485}$ is diffuse reflectance measured at 485±5 nm, $Rd_{513}$ is diffuse reflectance measured at 513±5 nm, $Rd_{598}$ is diffuse reflectance measured at 598±5 nm, $Rd_{629}$ is diffuse reflectance measured at 629±5 nm, and the computed parameter value is represented by B4.

12. The method of claim 11, wherein the diffuse reflectance measured at 485±5 nm, 513±5 nm, 598±5 nm, and 629±5 nm is normalized with respect to reflectance in the infrared wavelength range (650-750 nm) where absorption of blood is negligible.

13. The method of claim 9, further comprising:
placing the reflectance probe in close proximity to the tissue surface at one of said sampling sites and then carrying out said measuring; and
lifting the reflectance probe (pull-back) from said close proximity to the tissue surface to a distance where the reflectance probe no longer shadows the tissue and then repeating said measuring.

14. The method of claim 13, wherein the lifting is repeated at least once for a tissue spot, said measuring being repeated after each lifting.

15. The method of claim 9, wherein the blue light range is 470-520 nm, and the red light range is 590-650 nm.

16. The method of claim 9, wherein said directing light from the source to the area of esophageal tissue comprises directing light through a light guide of the endoscope.

17. A method for identifying malignancies in Barrett's Esophagus using white light endoscopy, comprising:
directing light from a source to a tissue with an endoscope to provide wide field illumination of a surface of the tissue, the light having a wavelength range that includes at least a portion of the visible spectrum;
measuring, with a reflectance probe, intensity of diffusely reflected light in at least four distinct narrow wavelength bands at different tissue sampling sites, said at least four bands being in the wavelength range of the illumination light, two of said bands being in the blue light range, and two of said bands being in the red light range;
determining a parameter value for each of the different tissue sampling sites, the parameter being a predetermined linear discriminate function based on said intensity measurements; and
discriminating between Barrett's Esophagus and dysplasia at the different tissue sampling sites based on the parameter values.

18. The method of claim 17, wherein the at least four distinct narrow wavelength bands include the wavelengths 485±5 nm, 513±5 nm, 598±5 nm, and 629±5 nm.

19. The method of claim 18, wherein the discriminate function is $$B4 = -14.32 + 626.88*Rd_{485} - 721.31*Rd_{513} + 253.76*Rd_{598} + 75.16*Rd_{629},$$

wherein $Rd_{485}$ is diffuse reflectance measured at 485±5 nm, $Rd_{513}$ is diffuse reflectance measured at 513±5 nm, $Rd_{598}$ is diffuse reflectance measured at 598±5 nm, $Rd_{629}$ is diffuse reflectance measured at 629±5 urn, and the computed parameter value is represented by B4.

20. The method of claim 19, wherein the diffuse reflectance measured at 485±5 nm, 513±5 nm, 598±5 nm, and 629±5 nm is normalized with respect to reflectance in the infrared wavelength range (650-750 nm) where absorption of blood is negligible.

* * * * *